United States Patent [19]
Taheri

[11] Patent Number: 5,327,913
[45] Date of Patent: Jul. 12, 1994

[54] PERCUTANEUS CARDIOMYOPLASTY METHOD

[76] Inventor: Syde A. Taheri, 1275 Delaware Ave., Buffalo, N.Y. 14209

[21] Appl. No.: 857,172

[22] Filed: Mar. 25, 1992

[51] Int. Cl.$^5$ .............................................. A61B 17/00
[52] U.S. Cl. ...................................... 128/898; 604/51
[58] Field of Search ................................. 604/51–53; 600/37; 623/1; 128/898

[56] References Cited

U.S. PATENT DOCUMENTS 4,778,787 10/1988 Castimpoolas et al. ............... 514/25

Primary Examiner—Jerome L. Kruter
Attorney, Agent, or Firm—Lieberman & Nowak

[57] ABSTRACT

Cardiomyoplasty can be performed without significant incisions by using muscle segments as patches to reinforce the defective myocardium. This method involves the use of a dilator to form an opening within the diaphragm to provide an opening through which to pass the greater omentum. The greater omentum is partitioned and brought to the myocardium via the opening in the diaphragm to serve as an extra blood supply. Muscle segments are then used as patches on the defective myocardium by implacing them between the greater omentum and the myocardium. This method is accomplished through the use of a needle shaped myoplasty instrument for obtaining the muscle segments and a specially constructed dilator for forming an opening in the diaphragm.

10 Claims, 5 Drawing Sheets

PERCUTANEUS CARDIOMYOPLASTY METHOD

BACKGROUND OF THE INVENTION

The present invention generally relates to methods of performing internal surgical procedures and to apparatus for performing such operations. More particularly, the invention relates to cardiac-operations for reinforcing the ventricle and improving the function of its wall by patching the myocardium with autogenous muscle segments and using the omentum as an extra blood supplier.

Cardiomyopathy is a common disorder. Many thousands of cases are reported yearly and thousands die of cardiomyopathy every year in the United States. The most widely used method of treating this disorder includes inotropic diuretic and beta blocker. Recently the method has included utilizing trained autologous latissimus dorsi myoplasty which requires six months training by pacemaker. Therefore it is clear that time and major surgical procedures are drawn-backs of the existing technique for treatment of cardiomyopathy.

The present invention resolves a number of the aforesaid problems while providing major advantages over prior art methods. One object and significant advantage of the present invention is the ability to perform a cardiomyoplasty utilizing an autogenous, non-autogenous or gene feted free muscle without significant incisions in the chest and abdomen with their attendant blood loss, potential for infection and possible scars.

It is a further object of the present invention to patch the myocardium with integrated free autogenous, possible non-autogenous or gene feted isolated striated muscle segments by cardiomyoplasty to reinforce the ventricle and to improve the function of the diskenytic ventricular wall.

It is a still further object of the present invention simultaneously to bring the omentum up to the myocardium without severing its natural blood supply.

SUMMARY OF THE INVENTION

The invention provides a method of performing cardiomyoplasty. The method involves inserting a dilator into the abdomen through a laparoscope, where it is used for opening the diaphragm. It further involves the partitioning of the omentum without severing its natural blood supply and transferring the partitioned omentum to the plural cavity while preserving its blood supply. A chest grasping device, introduced through a thoracoscope, is passed through the plural cavity and led through the opening in the diaphragm where it is connected to the omentum. After the omentum is partitioned, the chest grasping device with the attached omentum is retrieved through the diaphragm to the plural cavity and further up to the myocardium.

Muscle segments which have been obtained from a striated muscle are introduced through the chest thoracoscope. The segments are placed as patches on the myocardium and covered by the omentum in such a way that the cardiomyoplasty patches are placed in between the omentum and the myocardium.

The invention further comprises two instruments which are useful for performing the above-described method.

The first is an instrument for obtaining the muscle segments comprising a needle portion having a passageway through its center and a side opening connected to the passageway. Proximate to the side opening of the needle portion is a joint fixedly mounted to the needle portion. A blade, which at least partially fits into the side opening when in a close position, is rotatably connected to the joint. A control means is located in the passageway and functions as the moving mechanism for opening and closing the blade.

The second instrument used in the surgical procedure is a dilator having a longitudinal central member and an opening member slidably attached to the central member to permit forward or backward movement along the central member. By exerting force to its rear end, the opening member is converted from a closed to an open position. A stop means is fixedly attached to the central member preventing forward movement of the opening member along the central member while it is being opened.

BRIEF DESCRIPTION OF THE DRAWINGS

A description of the invention will be rendered by reference to the specific embodiment illustrated in the appended drawings. It is understood that these drawings depict only one typical embodiment of the invention and are not to be considered a limitation of its scope.

DETAILED DESCRIPTION OF THE INVENTION

Figure 1:
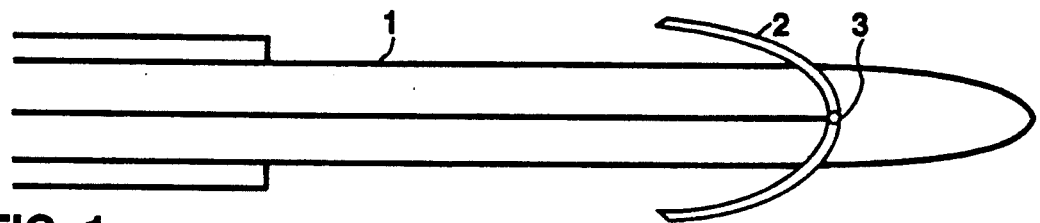
FIG. 1 is an enlarged side view of a myoplasty instrument (MI), depicted with its blades in closed position.

The invention relates to internal surgical procedures, such as cardiomyoplasty, performed without incisions where muscle segments are used as patches to reinforce the defective organ. One step comprises partitioning a blood supplier of the subject, for example, the omentum or another intestinal blood supplier, without severing its natural blood supply and transferring the partitioned blood supplier to wherever it is needed, in case of cardiomyoplasty to the plural cavity.

If the blood supplier is needed in the upper part of the subject and comes from the lower part, which is the case in a cardiomyoplasty operation, it needs to get past the diaphragm and into the plural cavity. To get the blood supplier to the plural cavity it is necessary to make an opening in the diaphragm and pass the blood supplier through. In order to facilitate the opening of the diaphragm this is first perforated, e.g., by small cauteries inserted through a laparoscope (1 in FIG. 11) that serves as a thruway tube. A dilator is passed into the diaphragm through a laparoscope, and activated to provide the opening, as shown in FIGS. 6 through 10. The dilator is retrieved through the laparoscope or thoracoscope leaving an opening in the diaphragm.

A chest grasping device is introduced into the plural cavity through a thoracoscope (2 in FIG. 11) which serves as a thruway tube. The grasping device is passed through the opening in the diaphragm where it is attached to the subject's blood supplier, e.g., the greater omentum, and holds this while the blood supplier is measured and divided, e.g. with the use of a camera and laser, which are also introduced into the subject through a thoracoscope (3 FIG. 11).

The chest grasping device with the blood supplier attached is then transferred to wherever the blood supply is needed. In cardiomyoplasty operations it is retrieved through the dilated diaphragm and brought into the plural cavity, where it is moved to the subject's myocardium.

The procedure further involves obtaining the appropriate autogenous, non-autogenous or gene feted striated muscle segments that serve as patches on the defective organ.

The muscle segments can be obtained by methods known to those skilled in the art or by the below described myoplasty instrument. The segments are thereafter reintroduced into the subject through a thoracoscope (2 in FIG. 11), and are placed on the defective organ (in a cardiomyoplasty operation, on the myocardium of the subject) to serve as patches.

To supply blood and maintain the muscle segments in place, the defective organ is covered with a blood supplier in such a way that the patches are placed in between the defective organ and the blood supplier. All these steps can be performed through a thoracoscope.

The invention also provides an instrument used in the procedure to obtain the muscle segments. This instrument has a needle portion which may be fabricated from stainless steel or some other material suited for use in internal surgical procedures. The needle portion has a passageway through its center and a side opening connected to the passageway, large enough to contain the cut muscle segments. A joint is fixedly mounted to the needle portion proximate to the side opening, and a blade, long and sharp enough to cut the muscle segments which under normal circumstances are between 2½ to 5 centimeters, is rotatably connected to this joint and capable of at least partially fitting into the side opening when in a closed position.

In other embodiments of the invention, the needle portion of the instrument may have a plurality of side openings and blades or, as shown in FIGS. 1 through 5, two diametrically opposite side openings and two diametrically opposite blades.

The mechanism for opening and closing of the blades to cut the desired muscle segment is located in the passageway. This mechanism is a central member (1 in FIGS. 1 through 5) having a front and a back end, the front end being connected to either the blades or the joint, and the member being capable of controlling the blades as they cut the muscle segments. In the simplest embodiment, the central member may be a cable where the cable's forward movement causes the blades to either open or close and the cable's backward movement causes the reverse action. It is contemplated that the central member may be rod, spring, bar or wire. The central member may also be an electrical circuit comprising a switch, actuator, or the like connected directly or indirectly to the blades or joint and a control or signalling device at the back, electrically (or mechanically) connected to the switch, actuator, or the like.

A plunger can further be fixedly attached to the central member facilitating the operation of the blades from the outside. Like the central member, the plunger may be an electronic or mechanical device and may comprise various arrangements well known to those skilled in the art as long as the plunger permits control over the operation of the blades through the central member. A needle carrier, e.g., plastic tubing or other appropriate material, may be provided as a sheath for the instrument.

Figure 2:
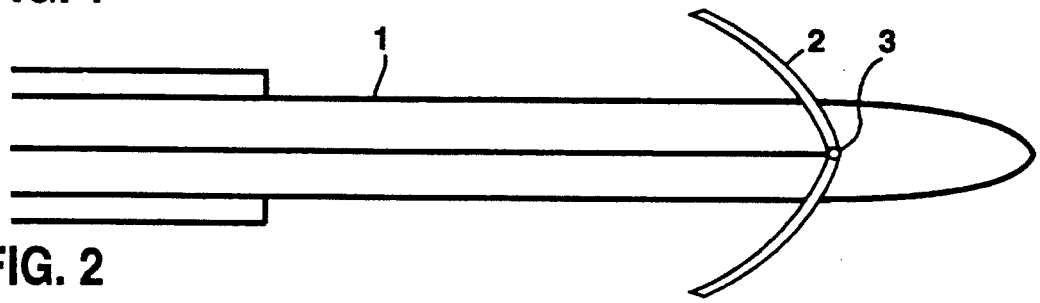
FIG. 2 is a side view of the embodiment of the MI illustrated in FIG. 1 in which the MI is depicted with activated blades.
Figure 3:
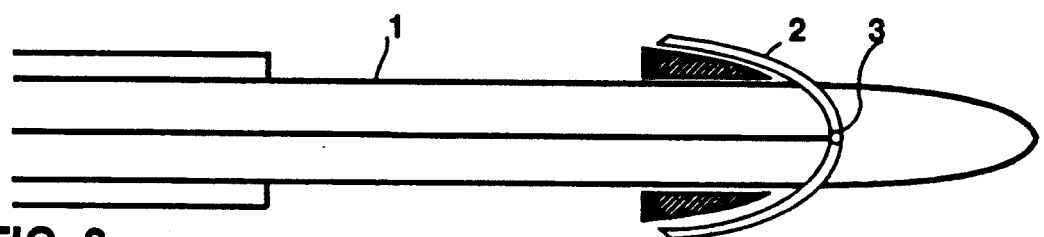
FIG. 3 is a side view of the MI shown in FIG. 1 in which the MI has excised the muscle fibers needed for the implantation.

The method of obtaining the desired muscle segment using this instrument comprises inserting the needle with the needlepoint first (9 in FIGS. 1 through 5) into the desired muscle and activating the blade(s) by use of the plunger or the central member. The instrument, also called the myoplasty instrument (MI), may be used in two alternative ways. In the first as shown in FIGS. 1 through 3, the instrument is inserted into the muscle with the blades pointing backwards the central member or plunger is then pushed backward so that the cutting blades (2) connected to the central member (1) by the joint (3) are opened. The MI is pulled back with the cutting blades (2) in their opened position, FIG. 2. By the reversed proceedings the blades are closed, FIG. 3, thereby cutting the wanted segments of the muscle which are trapped between the cutting blades (2) and the central member (1) within the openings (4).

Figure 4:
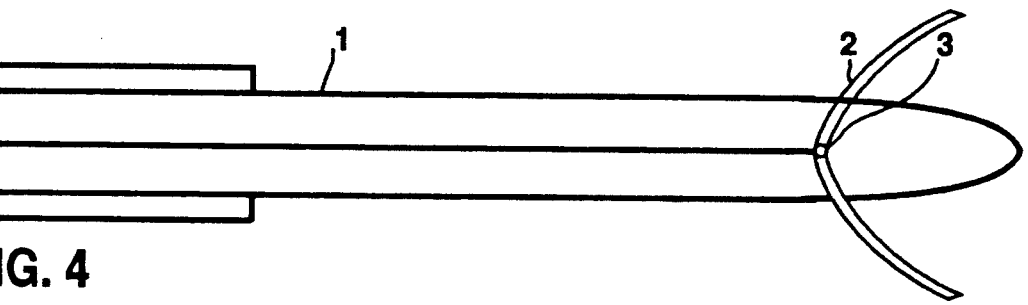
FIG. 4 is an enlarged side view of the MI in which it is depicted in its passive position with its blades aiming towards the needle point.
Figure 5:
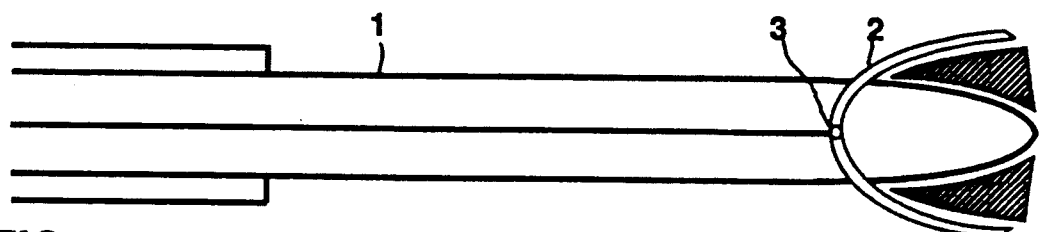
FIG. 5 is a side view of the embodiment of the MI illustrated in FIG. 4 in which the excision of muscle segments is accomplished and the cutting blades closed.
Figure 6:
FIG. 6 is an enlarged side view of the dilator's central member.

Another procedure for obtaining the needed muscle segments is shown in FIGS. 4 and 5. Here the instrument is inserted with the cutting blades (2) pointing forward. The plunger is then pulled backward, to cut the muscle segments.

Figure 11:
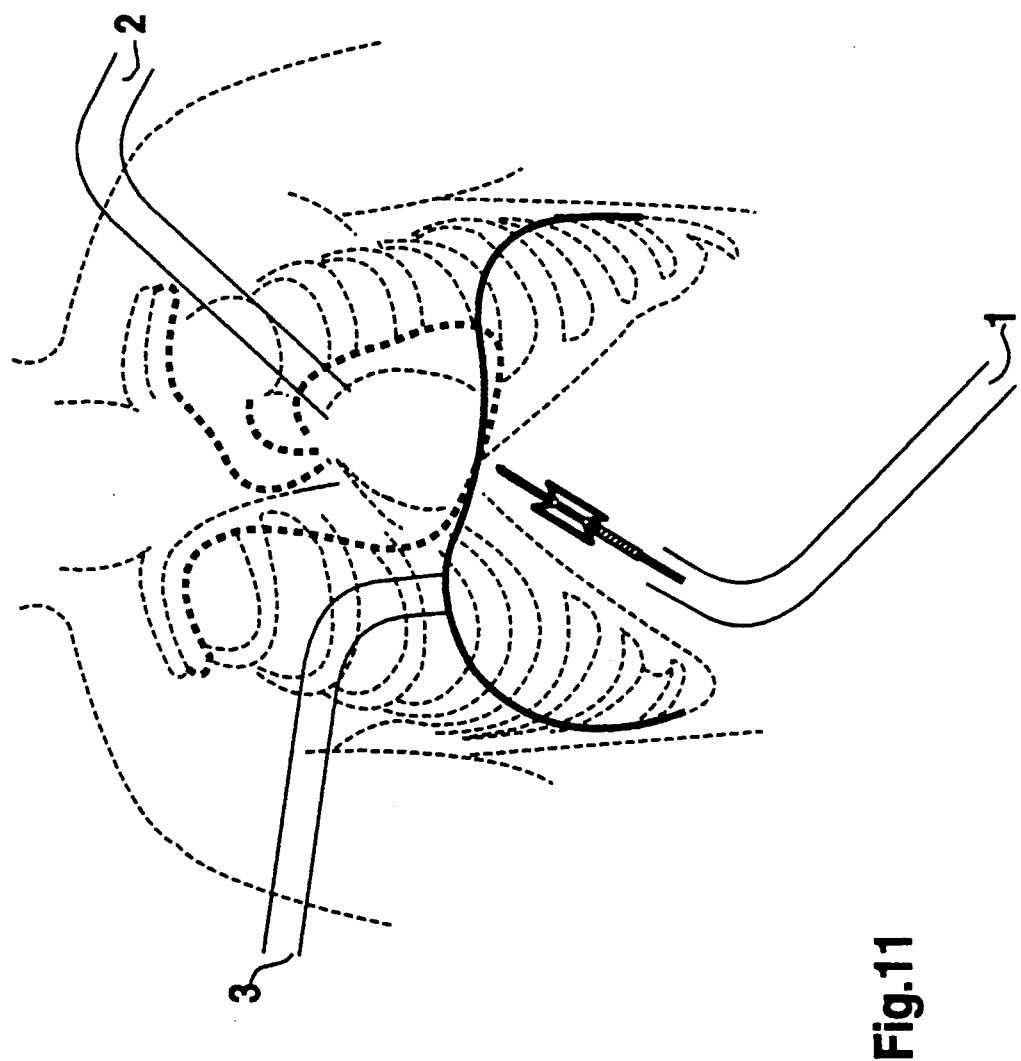
FIG. 11 is a schematic front view of a human body showing the approximate placement of the thoracoscope and the laparoscope.
Figure 12:
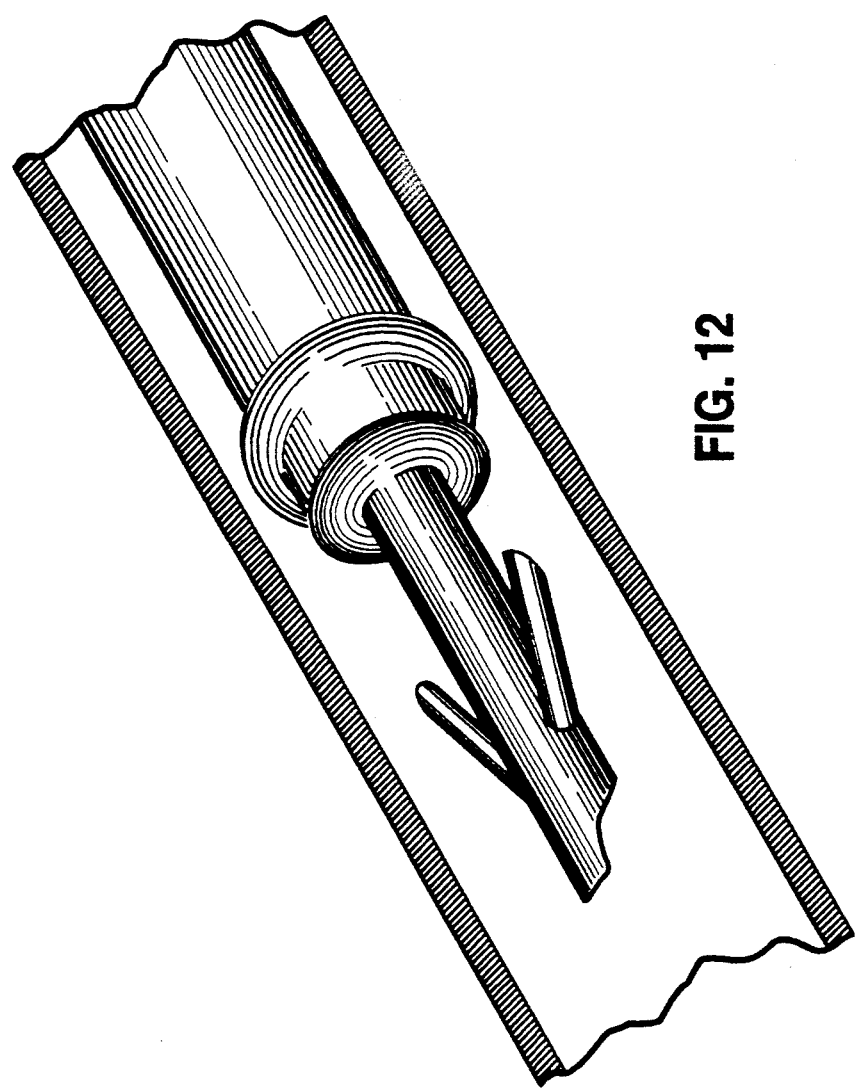
FIG. 12 is an enlarged view of an instrument used in obtaining muscle segments.
Figure 13:
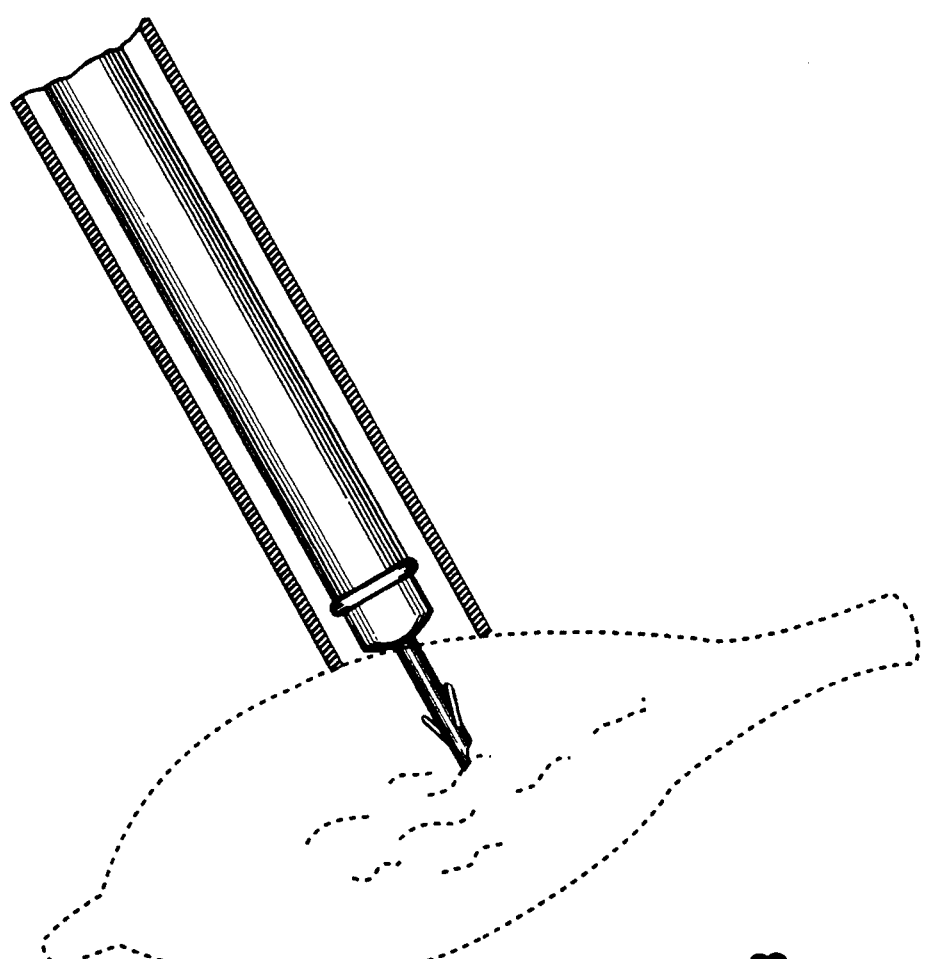
FIG. 13 is a schematic view of the surgical operation in which the instrument illustrated in FIG. 12 is used in obtaining a muscle segment.

With the blades trapping the muscle segments in the side openings, the MI is withdrawn from the muscle and the muscle segments are ready for being re-inserted through the chest thoracoscope (FIG. 11(3)). In case of a cardiomyoplasty, the muscle segments provide the (autogenous) cardiomyoplasty patches to the myocardium.

The invention also provides a second instrument, a dilator, useful in the above described cardio myoplasty procedure if the blood supplier needs to be transferred from underneath the diaphragm to the plural cavity.

The dilator comprises a relatively rigid longitudinal central member such as a rod, bar, tubing or guidewire (FIG. 6), which is flexible enough to allow it to pass through a laparoscope. This central member has a forward and a back end with the forward end optionally shaped as a hook (FIGS. 6 through 10). In other embodiments a hook or some other grasping device may be attached.

The dilator further comprises a relatively rigid opening member somewhat shorter than the central member and again flexible enough to allow the dilator to pass through the laparoscope. The opening member has a front and rear end, and is slidably attached to the central member to permit forward or backward movement along the central member.

Figure 7:
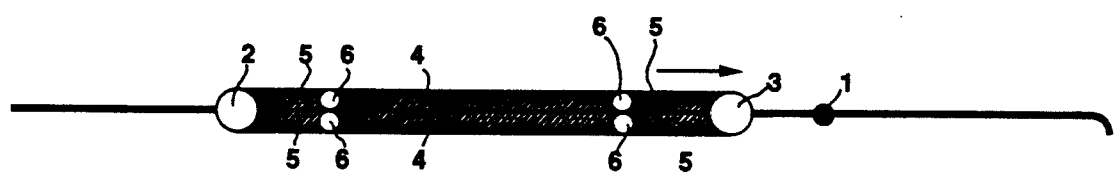
FIG. 7 is an enlarged side view of the opening member fixedly attached to the central member.

The opening member is opened from a closed position to its opened position by application of a force to either the front or rear end. In the preferred embodiments, the opening member comprises a plurality of relative rigid members and joints, each rigid member connected through a joint to another rigid member and thereby forming a continuous structure (FIG. 7). In the embodiment shown in the figures, the opening member includes two main joints (2 and 3 in FIGS. 7 through 10) slidably mounted on the central member; one at its front and, the other at the rear end. Each main joint is connected through rigid members (5 in FIGS. 7 through 10) and joints (6 in FIGS. 7 through 10) to primary rigid members (4 in FIGS. 7 through 10) which are substantially parallel to the central member when the opening member is fully opened or fully closed.

Figure 8:
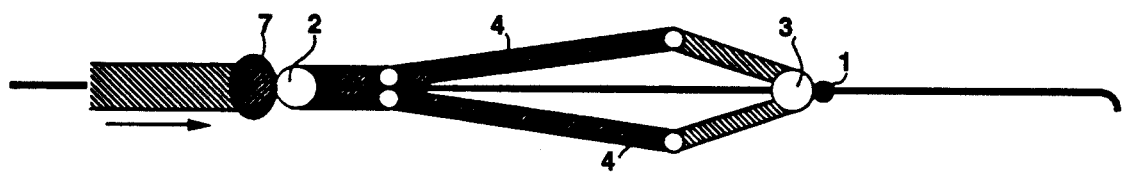
FIG. 8 is an enlarged side view of the opening members being opened slightly by a force pushing them towards the stop bear.
Figure 9:
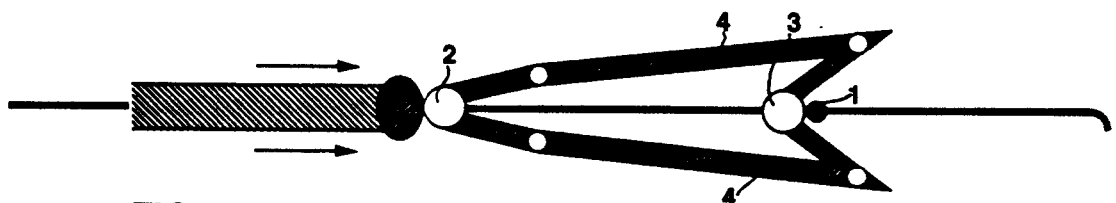
FIG. 9 is an enlarged side view of the opening members position after further opening has occurred.
Figure 10:
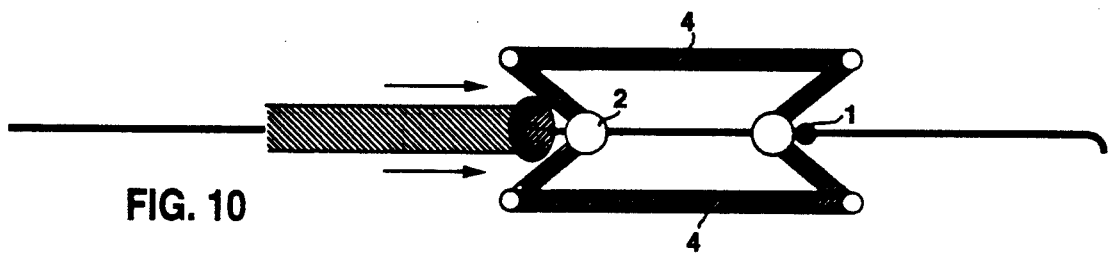
FIG. 10 is an enlarged side view of the opening members being fully opened.

The means used to open and close the dilator, may comprise a plunger slidably mounted on the central member which is capable of pushing forward the main joint of the rear end of the opening member (7 in FIGS. 8 through 10). It is also contemplated that the opening member may be open by a cable or the like attached to the main joint at the forward end and pulled back.

The dilator also comprises a stop means (1 FIGS. 6 through 10), which may be a knob or a bead which is fixedly attached to the central member. In embodiments where a plunger is applied as force to the rear end of the opening member, the stop means is closer to the forward end than the back end of the central member. In such embodiments, the stop means prevents forward movement of the opening member along the central member during opening. In other embodiments the stop means is at the back end of the central member and prevents backward movements.

What is claimed is:

1. A method of performing a surgical procedure for the reinforcement of a defective organ in a subject which comprises:
   i) partitioning the subject's omentum without severing omentum blood supply;
   ii) transferring the partitioned omentum to the vicinity of the defective organ while preserving its blood supply;
   iii) utilizing the partitioned omentum as a blood supply for a muscle segment; and
   iv) utilizing the muscle segment as a patch to reinforce the defective organ.

2. A method of claim 1 wherein transferring the omentum comprises making an opening in the diaphragm and moving the omentum through the opening.

3. A method of claim 2 wherein a dilator is introduced into the abdomen and a grasping device is introduced into the plural cavity, the dilator is used to provide an opening in the diaphragm, the grasping device is attached to the omentum, and said device with attached omentum is lifted into the plural cavity.

4. A method of claim 3 wherein introducing the dilator is by means of a laparoscope.

5. A method of claim 3 wherein introducing the grasping device is by means of a thoracoscope.

6. A method of claim 1 wherein the myocardium is reinforced.

7. A method of performing a surgical procedure for the reinforcement of a defective organ in a subject's plural cavity which comprises:
   i) inserting a laparoscope and dilator into the abdomen, said laparoscope being a thruway tube for the diaphragm;
   ii) passing the dilator to dilate the diaphragm and provide an opening;
   iii) activating the dilator to dilate the diaphragm and provide an opening;
   iv) introducing a thoracoscope and chest grasping device into the plural cavity, said thoracoscope being a thruway tube for the grasping device;
   v) leading said grasping device through the opening in the diaphragm;
   vi) dilate diaphragm for passage of the divided greater omentum;
   vii) connecting the grasping device to the subject's omentum;
   viii) partitioning said omentum; and
   ix) retrieving said chest grasping device with attached omentum through the dilated diaphragm to the plural cavity and further up to the subject's defective organ.

8. The method as set forth in claim 7 further characterized by the steps of:
   i) obtaining appropriate music segments;
   ii) reintroducing the obtained muscle segments through a chest thoracoscope;
   iii) placing said muscle segments on the defective organ of the subject as a patch; and
   iv) covering the defective organ with the omentum in such a way that said patch is between the omentum and defective organ.

9. A method of claim 7 wherein the myocardium is reinforced.

10. A method of cardiomyoplasty in a subject, which comprises:
   (a) partitioning the subject's omentum without severing the omentum blood supply;
   (b) making an opening in the diaphragm by using a dilator comprising:
      (i) a longitudinal central member having a forward end and aback end,
      (ii) an opening member having a front and rear end, which is slidably attached to the central member to permit forward or backward movement along the central member, the central member being capable of opening from a closed position to an open position by application of a force to its front or rear end,
      (iii) stop means fixedly attached to the central member for preventing movement of the opening member along the central member, and
      (iv) means for opening the opening member;
   (c) transferring the partitioned omentum to the plural cavity through the opening in the diaphragm, while preserving the omentum's blood supply;
   (d) obtaining a muscle segment from the subject using an instrument comprising:
      (i) a needle portion having a passageway through its center and a side opening connected to the passageway,
      (ii) a joint fixedly mounted to the needle portion proximate to the side opening,
      (iii) a blade rotatably connected to the joint and capable of at least partially fitting into the side opening when in a closed position, and (iv) control means located in the passageway and capable of moving the blade from a closed position to an open position;

(d) placing the muscle segment on the myocardium of the subject; and
(e) covering the myocardium with the omentum in such a way that the muscle segment is placed between the omentum and the myocardium.

* * * * *